United States Patent
Yakovlev et al.

(10) Patent No.: US 12,025,616 B2
(45) Date of Patent: *Jul. 2, 2024

(54) METHOD AND COMPOSITION FOR DETECTION OF PROTEOLYTIC PRODUCTS AND DIAGNOSIS OF MALIGNANT NEOPLASTIC DISEASE

(71) Applicants: Vasily Nikolaevich Yakovlev, Moscow (RU); Rustam Raisovich Suleimanov, Moscow (RU)

(72) Inventors: Vasily Nikolaevich Yakovlev, Moscow (RU); Rustam Raisovich Suleimanov, Moscow (RU)

(73) Assignees: Rustam Raisovich Suleymanov, Moscow (RU); EVGENY IOSIFOVICH GOUFMAN, Moscow (RU)

( * ) Notice: Subject to any disclaimer, the term of this patent is extended or adjusted under 35 U.S.C. 154(b) by 177 days.

This patent is subject to a terminal disclaimer.

(21) Appl. No.: 17/679,493

(22) Filed: Feb. 24, 2022

(65) Prior Publication Data

US 2022/0187303 A1  Jun. 16, 2022

Related U.S. Application Data

(63) Continuation-in-part of application No. 16/558,259, filed on Sep. 2, 2019, now abandoned, which is a continuation-in-part of application No. 15/304,896, filed as application No. PCT/RU2016/000573 on Aug. 25, 2016, now Pat. No. 10,444,236.

(30) Foreign Application Priority Data

Aug. 25, 2015 (RU) .......................... RU20150135793

(51) Int. Cl.
   *G01N 33/53*   (2006.01)
   *G01N 33/574*  (2006.01)
   *G01N 33/68*   (2006.01)
   *G01N 33/86*   (2006.01)

(52) U.S. Cl.
   CPC ... *G01N 33/57488* (2013.01); *G01N 33/6812* (2013.01); *G01N 33/6854* (2013.01); *G01N 33/86* (2013.01); *G01N 2333/968* (2013.01); *G01N 2333/972* (2013.01)

(58) Field of Classification Search
   None
   See application file for complete search history.

(56) References Cited

U.S. PATENT DOCUMENTS

| | | | |
|---|---|---|---|
| 10,444,236 B2* | 10/2019 | Yakovlev | G01N 33/57434 |
| 2012/0009650 A1* | 1/2012 | Koepf | C12N 9/6435 |
| | | | 530/380 |
| 2013/0217647 A1* | 8/2013 | Shuster | A61K 31/7072 |
| | | | 435/7.1 |

OTHER PUBLICATIONS

Harpel et al., Binding and Activation of Plasminogen on Immobilized Immunoglobulin G, The Journal of Biological Chemistry, vol. 264, No. 1, Jan. 1989, pp. 616-624 (Year: 1989).*

Wistedt et al., Kringle 2 Mediates High Affinity Binding of Plasminogen to an Internal Sequence in Streptococcal Surface Protein PAM, The Journal of Biological Chemistry, vol. 273, No. 38, Sep. 1998, pp. 24420-24424. (Year: 1998).*

* cited by examiner

*Primary Examiner* — Gary Counts
(74) *Attorney, Agent, or Firm* — Nadya Reingand

(57) ABSTRACT

Tumor invasion and metastasis is accompanied by significant activations of specific proteolysis enzymes. Tumor area is known to have increased infiltration of immunoglobulins G ("IgG"), so IgG may undergo proteolysis in this area. Serine proteases usually cleave peptide bonds between positively charged amino acids lysine and arginine. Since the intact PLG molecules as well as its fragments have lysine binding sites, they can bind to damaged IgG or fragments thereof with free C-terminal lysine that can appear in a circulation after proteolysis in the malignant tumor area. In the present invention we demonstrated the increased binding of damaged IgG or fragments thereof with free C-terminal lysine to fragments of PLG in samples from patients with breast cancer, ovarian cancer, lung cancer, colorectal cancer, prostate cancer vs. samples from healthy donors, and thus we proposed a novel diagnostic method.

9 Claims, No Drawings
Specification includes a Sequence Listing.

METHOD AND COMPOSITION FOR DETECTION OF PROTEOLYTIC PRODUCTS AND DIAGNOSIS OF MALIGNANT NEOPLASTIC DISEASE

CROSS-REFERENCE TO RELATED APPLICATIONS

The present patent application is a Continuation-in-Part of U.S. patent application Ser. No. 16/558,259, filed Sep. 2, 2019, abandoned on Feb. 25, 2022, which is a Continuation-in-Part of U.S. patent application Ser. No. 15/304,896, filed Oct. 18, 2016, now U.S. Pat. No. 10,444,236, issued on Sep. 25, 2019, which is a National stage application from PCT Application PCT/RU2016/000573, filed Aug. 25, 2016, now expired, which claims priority to Russian Patent Application RU20150135793, filed Aug. 25, 2015, now Russian Patent No. 2597782, issued on Aug. 24, 2016, all of which are incorporated herein in their entireties.

REFERENCE TO A SEQUENCE LISTING

SEQ ID NO: 1 through SEQ ID NO: 7, incorporated fully by reference herein, are provided in ASCII format together in one separately enclosed .TXT file, submitted via EFS-Web—File name: SequenceListing_CIP from16-558259.txt; Date of Creation: Feb. 16, 2022; File size: 17.2 KB.

FIELD OF THE INVENTION

The present invention relates to the detection of malignant neoplastic disease. The invention relates particularly to immunological diagnostic methods that utilize the full-length molecule of plasminogen, or fragments thereof, which may be used as universal detectors of proteolytic products of immunoglobulins G ("IgG") having a free C-terminal lysine. Furthermore, it relates to a composition and a method for an improved detection of malignant neoplastic disease, as well as diagnostic and/or prognostic uses.

BACKGROUND OF THE INVENTION

Tumor invasion and metastasis is accompanied by significant activations of specific proteolysis enzymes. This process leads to proteolytic degradation of the extracellular matrix. The serine proteases of the plasminogen activation proteolytic cascade are well known to play an important role in the process of tumor cell invasion.

Serine proteases usually cleave peptide bonds between the positively charged amino acids lysine and arginine, as well as the esters and amides of these amino acids. To date, some authors have shown that the products of proteolytic activity can serve as a universal marker, the detection of which is associated with oncogenic processes. There exists data of the specific proteolysis of immunoglobulins by plasmin (See Peter S.Harpel et al., The Journal of Biological Chemistry Vol. 264, No. 1, Issue of January 5, pp. 616-624 (1989)). Following cleavage, the IgG fragments were shown to specifically interact with plasminogen due to the presence of a C-terminal lysine. IgG fragments that bind to plasminogen were treated with carboxypeptidase B, which specifically cleaves only C-terminals lysine and arginine. After this treatment, the proteins lost their ability to bind to plasminogen, indicating that C-terminal lysine participation is essential for the binding to plasminogen and its fragments. Plasminogen has 5 domains, referred to as "kringles" (K1, K2, K3, K4, and K5), which have a strong affinity for lysine. Each kringle has a strong conservative aminoacid amino acid sequence —Asn-Tyr-Cys-Arg-Asn-Pro-Asp (SEQ ID NO: 7)— which is a special attribute of kringles of plasminogen.

Since the intact plasminogen molecules as well as its fragments have lysine binding sites, they can bind to proteins with a C-terminal lysine and be used for detection of damaged IgG or IgG fragments in a circulation that appears after proteolysis in the malignant tumor area. These detectors have universal properties compared with other proposed methods of detecting degradation products which require using specific monoclonal antibodies for each product of proteolysis.

Accordingly, it is an object of the present invention to provide means and methods to perform accurate and less biased diagnostic tests in a simple and efficient way for routine testing when diagnosing or prognosing malignant neoplastic diseases.

SUMMARY OF THE INVENTION

Increased levels of the damaged IgG and/or fragments with a free C-terminal lysine thereof can serve as diagnostic markers of diseases associated with elevated levels of damaged IgG and/or fragments with a free C-terminal lysine thereof. The present invention describes a new method for detection of the damaged IgG and/or fragments with a free C-terminal lysine thereof in a biological fluid. The invention also comprises a diagnostic test system (e.g., kit) for identifying subjects with a high concentration of the damaged IgG and/or fragments with a free C-terminal lysine thereof. This diagnostic test system is comprised of:

The ligand—a fragment of human plasminogen comprised of one sequence of SEQ ID NO: 1-4 (Table 1), at least, including the negative control sample (NC) and positive control sample (PC). The damaged IgG and/or fragments with a free C-terminal lysine thereof bind to fragments of human plasminogen comprised of one sequence of SEQ ID NO: 1-4, and the damaged IgG and/or fragments with a free C-terminal lysine thereof may be detected using, e.g., an immunoassay technique. One aspect of the present invention is a method for detecting damaged IgG and/or fragments with a free C-terminal lysine thereof in a biological sample, in vitro, the method comprising the steps of:

a) contacting said biological sample with a composition comprising at least one of the four sequences listed in Table 1 (SEQ1-SEQ4) wherein damaged IgG or fragments with a free C-terminal lysine thereof bind to the at least one of four above sequences, and b) detecting complexes with damaged IgG or fragments with a free C-terminal lysine thereof.

Accordingly, a differential presence of the damaged IgG or fragments with a free C-terminal lysine thereof found in a given biological sample provides useful information regarding the probability of whether a subject being tested has malignant neoplastic diseases, such as but not limited to lung cancer, breast cancer, colorectal cancer, and ovarian cancer. The probability that a subject being tested has a malignant neoplastic disease depends on whether the quantity of the damaged IgG or fragments with a free C-terminal lysine thereof, in a test sample taken from said subject, are statistically significant from a quantity of the damaged IgG or fragments with a free C-terminal lysine thereof in a biological sample taken from healthy subjects, or alternatively statistically significant from a control level known to exist in healthy subjects.

DETAILED DESCRIPTION OF PREFERRED EMBODIMENTS

Definitions.

Technical and scientific terms used in the description have the same meaning and value that are commonly used in the relevant areas of science and technology, except as further indicated herein below.

The term "antigen", as used herein, refers to a protein or fragments of a protein, capable of binding antibodies.

The term "ligand", as used herein, refers to a peptide sequence capable of binding to a free C-terminal lysine.

The term "kringle", as used herein, refers to a protein domain having a structure stabilized by three disulfide bonds and having a strong conservative amino acid sequence—Asn-Tyr-Cys-Arg-Asn-Pro-Asp, or its equivalents.

The term "domain", as used herein, refers to a part of a protein characterized by certain structural or functional properties.

The term "analysis", as used herein, refers to methods of identifying the molecular compounds, comprising the steps of: (a) the interaction with the antigen within a biological sample under suitable conditions to form an antigen-antibody complex; and (b) the detection of these complexes.

The term "marker", as used herein, refers to particular molecular compounds of a specific structure, the presence of which, in human tissue samples, is associated with a specific range of diseases.

The term "epitope", as used herein, refers to a region of a protein molecule which is capable of interacting with the antibody.

The term "detector", as used herein, refers to a protein molecule which is capable of forming a non-covalent bond with another protein molecule.

The term "diagnostic test", as used herein, refers to the detection of a diagnostic determinant using a specific laboratory method, the analytical parameters of which remain constant.

The term "subject", as used herein, includes humans, non-human primates, such as but not limited to chimpanzees and other ape and monkey species, farm animals such as but not limited to cattle, sheep, pigs, goats, and horses, domestic mammals such as but not limited to dogs and cats, laboratory animals including but not limited to rodents such as but not limited to mice, rats, and guinea pigs. The term does not denote a particular age or sex. Thus, adult and newborn subjects, as well as fetuses, whether male or female, are intended to be covered. In preferred embodiments, the subject is a mammal, including humans and non-human mammals. In the most preferred embodiment, the subject is a human.

The term "healthy", as used herein, refers to a subject possessing good health. Such a subject demonstrates an absence of any malignant or non-malignant disease. In the context of this application, a "healthy individual" is only healthy in that they have an absence of any malignant or non-malignant disease. A "healthy individual" may have other diseases or conditions that would normally not be considered "healthy".

The term "biological sample", as used herein, encompasses a variety of sample types obtained from any subject having or not having malignant neoplasm. A typical subject is a human; however, any mammal that has a malignant neoplasm that may develop cancer can serve as a source of a biological sample useful in the disclosed methods. Exemplary biological samples useful in the disclosed methods include but are not limited to clinical samples, cells in culture, cell supernatants, cell lysates, and body fluids. For example, biological samples include samples obtained from fluids collected from an individual suspected of having a malignant neoplasm. Examples of biological fluid samples include but are not limited to blood serum, blood plasma, lymph, exudates, feces, gastric acid, gastric juice, lymph, mucus, pericardial fluid, peritoneal fluid, pleural fluid, pus, saliva, sputum, synovial fluid, tears, sweat, vaginal secretion, vomit, and urine.

The terms "polypeptide," "protein," and "peptide", as used herein interchangeably, refer to amino acid chains in which the amino acid residues are linked by peptide bonds or modified peptide bonds. The amino acid chains can be of any length which is greater than two amino acids. Unless otherwise specified, the terms "polypeptide", "protein", and "peptide", also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular cross-linking and covalent attachment to various moieties such as lipids, flavin, biotin, polyethylene glycol or derivatives thereof, etc. In addition, modifications may also include cyclization, branching, and cross-linking. Furthermore, amino acids other than the conventional twenty amino acids encoded by genes may also be included in a polypeptide.

The term "lung cancer", as used herein, refers to a neoplasm, e.g., a malignant neoplasm, of the lung within a given subject, wherein the neoplasm is of epithelial origin (i.e., carcinoma of the lung). Lung carcinomas are categorized by the size and appearance of the malignant cells and the term "lung cancer" includes both non-small cell lung cancer (NSCLC) and small cell lung cancer (SCLC). The term "lung cancer" includes both localized and metastasized lung cancer. The term "lung cancer" can be qualified by the terms "localized" or "metastasized" to differentiate between different types of tumors, where "localized" refers to the original mother tumor, and "metastasized" refers to the tumors that have spread from the original mother tumor.

The TNM System (tumor, node, metastases), as referred to herein, may be used to stage NSCLC in an initial evaluation. Using the TNM descriptors, a group is assigned, ranging from occult cancer, through stages 0, IA (one-A), IB, MA, MB, IMA, NIB and IV (four). This stage group assists with the choice of treatment and the estimation of a prognosis.

For both NSCLC and SCLC, the two general types of staging evaluations are clinical staging and surgical staging. Clinical staging is performed prior to definitive surgery. It is based on the results of imaging studies (such as CT scans and PET scans) and biopsy results. Surgical staging is evaluated either during or after the operation, and is based on the combined results of surgical and clinical findings, including surgical sampling of thoracic lymph nodes.

The term "ovarian cancer", as used herein, refers to a neoplasm, e.g., a malignant neoplasm, of the ovary within a given female subject, wherein the neoplasm is of epithelial origin. The term "ovarian cancer" includes both localized and metastasized ovarian cancer. The term "ovarian cancer" can be qualified by the terms "localized" or "metastasized" to differentiate between different types of tumor, where "localized" refers to the original mother tumor, and "metastasized" refers to tumors that have spread from the original mother tumor.

Ovarian cancer can be staged according to the AJCC/TNM System. This describes the extent of the primary tumor (T), the absence or presence of metastasis to nearby lymph nodes (N), and the absence or presence of distant metastasis (M). The extent of primary tumor contains three subcategories, T1, T2, T3. This closely resembles the system that is actually used by most gynecologic oncologists, called the FIGO system. Both rely on the results of surgery for the actual stage. In the FIGO system the tumor stage is classified from Stage I-Stage IV (T1-T4) depending on how far the tumor has spread, where stage IV (T4) is worst, meaning that the tumor has spread to its estimated limit. Stages T1-T3 further contain the subcategories, A, B and C.

The term "breast cancer", as used herein, refers to a neoplasm, e.g., a malignant neoplasm, of the mammary gland within a given female subject, wherein the neoplasm is of epithelial origin. The term "breast cancer" includes both localized and metastasized breast cancer. The term "breast cancer" can be qualified by the terms "localized" or "metastasized" to differentiate between different types of tumor, where "localized" refers to the original mother tumor, and "metastasized" refers to tumors that have spread from the original mother tumor.

Breast cancer can be staged according to the AJCC/TNM System. This describes the extent of the primary tumor (T), the absence or presence of metastasis to nearby lymph nodes (N), and the absence or presence of distant metastasis (M). The extent of primary tumor contains four stages (I-IV), T1, T2, T3, and T4. Diagnosis relies on the results of surgery for the actual stage. Stage IV is worst, meaning that the tumor has spread to its estimated limit. Stages T1-T2, further contain subcategories, A, B, and T3 contain subcategories, A, B, C.

The term "colorectal cancer", as used herein, refers to a neoplasm, e.g., a malignant neoplasm, of the colon or rectum within a given subject, wherein the neoplasm is of epithelial origin. The term "colorectal cancer" includes both localized and metastasized colorectal cancer. The term "colorectal cancer" can be qualified by the terms "localized" or "metastasized" to differentiate between different types of tumors, where "localized" refers to the original mother tumor, and "metastasized" refers to tumors that have spread from the original mother tumor.

Colorectal cancer can be staged according to the AJCC/TNM System. This describes the extent of the primary tumor (T), the absence or presence of metastasis to nearby lymph nodes (N), and the absence or presence of distant metastasis (M). The extent of primary tumor contains four stages, each with three stages (I-III) T1, T2, T3. Diagnosis relies on the results of surgery for the actual stage. Stage IV is worst, meaning that the tumor has spread to its estimated limit. Stages T1-T2, further contain subcategories, A, B and T3 contain subcategories, A, B, C.

The term "prostate cancer", as used herein, refers to a neoplasm, e.g., a malignant neoplasm, of the prostate of a given subject, wherein the neoplasm is of epithelial origin. The term "prostate cancer" includes both localized and metastasized prostate cancer. The term "prostate cancer" can be qualified by the terms "localized" or "metastasized" to differentiate between different types of tumors, where "localized" refers to the original mother tumor, and "metastasized" refers to tumors that have spread from the original mother tumor.

Prostate cancer can be staged according to the AJCC/TNM System. This describes the extent of the primary tumor (T), the absence or presence of metastasis to nearby lymph nodes (N), and the absence or presence of distant metastasis (M). The extent of primary tumor contains four main categories, T1, T2, T3, and T4. Diagnosis relies on the results of surgery for the actual stage. Stages T1-T2 further contain subcategories, A, B, C. Stage T3 further contains the subcategories, A and B.

The preferred embodiments of the present invention are described in the following paragraphs.

The method for the preparation of the heavy chain, (Glu-H) Glu1-Arg561, and light chain (Glu-L), Val562-Asn791, of human plasminogen, is described as follows.

The basic method comprises the activation of plasminogen to plasmin, followed by the reduction of S—S bonds between heavy and light chains in conditions that exclude autolysis, then isolating the fragments using affinity chromatography on Lys-Sepharose 4B. Urokinase cleaves the Arg561-Val562 bond in plasminogen. The resulting plasmin cuts the 77-78 bond and cleaves off the N-terminal peptide (1-77). Mercaptoethanol reduces the two bonds between Cys558-Cys566 and Cys548-Cys666, which link the heavy and light chains.

First step: Glu-plasminogen is isolated from frozen human donor plasma by affinity chromatography on Lys-Sepharose 4B, at 4° C., and a pH of 8.0. Blood plasma is thawed in the presence of aprotinin, centrifuged for 30 min, at 4° C., and diluted 2-fold in a 0.02 M phosphate buffer, pH 8.0, containing 20 KIU/ml aprotinin. The prepared plasma is then applied onto a Lys-Sepharose 4B column, equilibrated with a 0.1 M K-phosphate buffer, pH 8.0, containing 20 KIU/ml aprotinin. The column is washed to remove unbound proteins with a 0.3 M phosphate buffer, pH 8.0, containing 20 KIU/ml aprotinin, overnight, to an absorbance at A280=0.05-0.01. Glu-plasminogen is eluted with a solution of 0.2 M 6-aminocaproic acid in a 0.1 M K-phosphate buffer, pH 8.0, containing 20 KIU/ml aprotinin. Fractions containing protein are pooled and subjected to further purification by precipitation $(NH_4)_2SO_4$ (0.31 g/ml protein solution). The precipitate is stored at 4° C. for 18-24 hours and then separated by centrifugation, and dissolved in a 0.05 M Tris-HCl buffer, pH 8.0, to a concentration of 1.5-2.0 mg/ml. The purified Glu-plasminogen is then dialyzed at 4° C. against water (pH 8.0), and lyophilized.

Second step: Urokinase is added to a final concentration of 600 IU/ml to a solution of Glu-plasminogen (5 mg/ml) in a 0.05 M Tris-HCl buffer, pH 8.8, containing 0.02 M L-lysine, 0.15 M NaCl, 20% glycerol, and 6,000 KIU/ml aprotinin, and incubated for 4 h at 37° C. The progression of conversion of Glu-plasminogen to plasmin is monitored by the hydrolysis of the specific substrate, S-2251 (HD-Val-Leu-Lys p-nitroanilide, Sigma, USA), by plasmin in samples from the reaction, with complete conversion identified by observation of the maximum conversion rate for the substrate.

Third step: This step described the reduction of S—S-bonds between the heavy and light chains of plasmin. Mercaptoethanol is added to the plasmin solution to a final concentration of 0.25 mM and incubated under nitrogen in the dark for 20 minutes at room temperature. The resulting free SH-groups are blocked by adding a freshly prepared solution of iodoacetic acid in a 0.1 M Na-phosphate buffer, pH 8.0 (to a final concentration of 0.315 M) and incubated for 20 minutes.

Fourth step: This step described the separation of the heavy and light chains of plasmin by column chromatography on Lys-Sepharose 4B. The reaction mixture is diluted to a concentration of 1 mg/ml of protein with 0.1 M Na-phosphate buffer, pH 8.0, containing 20 KIU/ml aprotinin and applied to a Lys-Sepharose 4B column, equilibrated with the same buffer. Chromatography is performed at 25° C. The heavy chain of plasmin, containing kringles K1-K4 and 30 amino acid residues of the connecting peptide, is adsorbed onto the sorbent. The light chain is washed away with the equilibration buffer. The heavy chain (MR~56-57 kDa) is eluted with a 0.2 M solution of 6-aminocaproic acid in a 0.1 M Na-phosphate buffer, pH 8.0. The pooled fractions are dialyzed against water (pH~8.0) and lyophilized.

The purity and molecular weight of the protein were assessed by 12% SDS-polyacrylamide gel electrophoresis. The absence of amidase activity (for S-2251) before and after incubation with urokinase confirmed that the solution of the heavy chain did not contain trace concentrations of miniplasminogen, which may go undetected by electrophoresis.

The purification of Lys-plasminogen (Lys78-Asn791) and its heavy chain (Lys-H Lys78-Arg561) may be performed by the same method, but without aprotinin.

a) The isolation of kringle domains K1-K4 (Tyr80-Ala440), K1-K3 (Tyr80-Val338), and K4-K5 (Val355-Phe546) was performed using elastase treatment of Glu-plasminogen by the method described in the work of Cao and colleagues (See Cao Y., Ji R. W., Davidson D., Schaller J., Marti D., Sohndel S., McCanse S. G., O'Reilly M. S., Llinas M., and Folkman J., J. Biol. Chem., 271, 29461-29467 (1996)). Glu-plasminogen was incubated with elastase at a ratio of 50:1 in a buffer containing 0.05 M Tris-HCl, pH 8.5, 0.5 M NaCl, and 200 KIU aprotinin, for 5 hours at room temperature. The reaction was stopped by adding PMFS to a concentration of 1 mM for 40-50 min. Gel-filtration on a Sephadex G-75 column was performed to separate low and high molecular weight proteins. Protein fractions of the second peak containing K1-3K, K1-K4, K4-K5, and miniplasminogen were applied to Lys-Sepharose 4B affinity column equilibrated with a buffer containing 0.05 M Tris-HCl, pH 8.5 and 0.15 M NaCl. After the removal of miniplasminogen which was not adsorbed onto the Lys-Sepharose 4B in the flow-through fraction, the adsorbed fragments K1-K3, K1-K4 and K4-K5 were eluted with a solution of 0.2 M 6-aminocaproic acid in the same buffer, dialyzed against a buffer containing 0.02 M Tris-HCl, pH 8.0, and applied to a column of heparin-agarose equilibrated with the same buffer. Unbound fragments K1-K4 and K4-K5 were eluted with 0.02 M Tris-HCl, pH 8.0,and fragment K1-K3 was eluted with a solution of 0.25 M KCl in the same buffer. The purified fragment K1-K3 was dialyzed against water and lyophilized. Fragments K1-K4 and K4-K5 were separated by gel filtration on Sephadex G-75. Kringle K1 (Tur80-Glu164) and K2-K3 (Cys165-Val338) were isolated from the K1-K3 (Tyr80-Val338) via treatment with pepsin (or proteases.aureus V8) with a further separation on Lys-Sepharose 4B and gel filtration on Sephadex G-75.

The production of a diagnostic test system (e.g., kit) for ELISA to assay damaged IgG or fragments with (i.e. having) a free C-terminal lysine thereof is described in the following paragraphs. The kit may be used to analyze the test subject's biological samples to perform any of the following non-exclusionary purposes:

i) detecting damaged IgG and/or fragments thereof with a free C-terminal lysine in a biological sample of lung cancer, breast cancer, colorectal cancer, ovarian cancer, and prostate cancer subjects;

ii) detecting lung cancer, breast cancer, colorectal cancer, ovarian cancer, and prostate cancer in a subject; or iii) diagnosing or prognosing lung cancer, breast cancer, colorectal cancer, ovarian cancer, and prostate cancer in the subject; or iv) predicting outcome of treatment of lung cancer, breast cancer, colorectal cancer, ovarian cancer, and prostate cancer in the subject; or v) assessing efficacy of treatment lung cancer, breast cancer, colorectal cancer, ovarian cancer, and prostate cancer in the subject; or vi) assessing recurrence lung cancer, breast cancer, colorectal cancer, ovarian cancer, and prostate cancer in the subject.

Enzyme-linked immunosorbent assay (ELISA), and sandwich ELISA, are immunoassays that are advantageously used in the methods disclosed herein. In an ELISA, an unknown amount of antigen is affixed to a surface, and then a specific antibody is applied over the surface so that it can bind to the antigen. This antibody is linked to an enzyme, and in the final step, a substance is added so that the enzyme can convert to some detectable signal, most commonly a colour change in a chemical substrate. In a sandwich ELISA, a capture antibody that can bind to the antigen is affixed to the surface. The other steps are equivalent to the ELISA. In an Enzyme Immuno Assay (EIA), which is similar to the sandwich ELISA, streptavidin is affixed to a surface and then the capture antibody is biotinylated, otherwise the other steps are performed equivalently as the ELISA.

When preparing a diagnostic system, fragments of plasminogen containing at least two kringle domains are used as the ligands for coating the solid phase. The various ligands used in ELISA are listed in Table 1. Their primary amino acid sequences are in the sequence listing.

TABLE 1

| peptide chain | Mass, kDa | Name | |
|---|---|---|---|
| $Glu^1$-$Arg^{561}$ | 65 | heavy chain (Glu-H) | SEQ ID NO: 1 |
| $Lys^{78}$-$Arg^{561}$ | 59 | heavy chain (Lys-H) | SEQ ID NO: 2 |
| $Lys^{78}$-$Pro^{447}$ | 58 | K1-4 ($Lys^{78}$-$Pro^{447}$) | SEQ ID NO: 3 |
| $Tyr^{80}$-$Val^{338}$ | 41 | K1-3 ($Tyr^{80}$-$Val^{338}$) | SEQ ID NO: 4 |
| $Cys^{165}$-$Val^{338}$ | 31 | K2-3 ($Cys^{165}$-$Val^{338}$) | SEQ ID NO: 5 |
| $Val^{355}$-$Phe^{546}$ | 22 | K4-5 (Val355-Phe546) | SEQ ID NO: 6 |

The ligand was diluted in a 0.1M carbonate-bicarbonate buffer, pH 9.6, at a maximum concentration of 5 microgram/ml.

PBS (phosphate buffered saline): 0.14M NaCl; 0.003M KCl: 0.005M $Na_2HPO_4$; 0.002M $KH_2PO_4$.

Washing solution: 0.05% TWEEN 20 (Polyethylene glycol sorbitan monolaurate, or Polysorbate 20) in PBS.

Substrate buffer (pH 4.3): 31 mM citric acid, 0.05 N NaOH, 3 mM $H_2O_2$.

TMB solution: 5 mM 3,3', 5,5'-tetramethylbenzidine in 70% DMSO.

Chromogenic substrate solution: 4 parts of substrate buffer mixed with 1 part TMB solution.

To create the immunoassay kit, the immobilization of the ligand is preliminarily performed on a solid phase. Various types of carriers for immobilization of a ligand can be used, including cellulose acetate, glass beads, or other particles that can adsorb proteins, as well as immunological plates or plastic strips.

100 microliters of the ligand solution is added to each well of a 96-well immunological plate (Costar). The solution is incubated for 14-16 hours at 4° C. in a humidified chamber. The contents of the wells are discarded. A blocking solution comprising 200 microliters of a 1% solution of bovine serum albumin (BSA) in PBS is added to the wells and incubated for 1.5 to 2 hours at room temperature. After incubation, the blocking solution is removed, the plate is dried overnight at room temperature and then may be used in further applications.

The test sample, negative control samples, and positive control samples are diluted300-fold with PBS with a 0.5% BSA buffer. 100 microliters of the solution are added to the appropriate wells and incubated for 1 hour at 37° C. After incubation, the solution is discarded, the plate is washed 4 times with the washing solution. 100 microliters of a working solution of the mice monoclonal antibodies to human IgG, conjugated with horseradish peroxidase (Angiogen LLC, Russian Federation), diluted in PBS with 0.5% BSA, is added to the appropriate wells and incubated for 1 hour at 37° C. Unbound components are discarded and the wells are washed with washing solution. 100 microliters of the chromogenic substrate-solution are then added to all the wells and incubated for 15 minutes at 37° C. The reaction is stopped by the addition of 100 microliters of a stop solution (e.g., 2M $H_2SO_4$). Photometry was performed on a "UNI-PLAN" photometer (Pikon, Russia) at a wavelength of 450 nm.

The negative control of concentration level of damaged IgG or fragments with a free C-terminal lysine thereof in ELISA may be performed as follows.

Five sera samples from healthy subjects are taken as negative controls; these were chosen so that the optical density (OD) of each one differed from the group mean by no more than 5% in ELISA. These 5 samples were pooled, and the resulting sample may be used as the negative control sample (NC), taken to indicate the normal (healthy) concentration level of damaged IgG or fragments thereof with a free C-terminal lysine. Dilution of mice monoclonal antibodies to human IgG conjugated with horseradish peroxidase was that OD of C ranged between 0.2 and 0.4. The samples with an OD exceeding that of the NC samples by more than 30% were considered positive. This cutoff range avoids false positives. Positive control (PC) was prepared from human IgG (Sigma-Aldrich) after plasmin treatment. Plasmin-treated IgG was prepared using human IgG by mixing 100 microliters of Lys-plasminogen (1 mg/ml) in PBS with 100 microliters of urokinase (500 IU/ml; Sigma-Aldrich) for 5 minutes, and 100 microliters of human IgG (1 mg/ml in PBS) were added, mixed, and incubated for 6 hours at 37° C. The reaction was stopped by adding of 50 microliters of aprotinin (10,000 IU/ml).

To demonstrate the involvement of C-terminal lysines in binding to plasminogen, the sera samples were diluted by PBS 100-fold and 100 microliters mixed with 2 microliters carboxypeptidase B (CPB; 5 mg/ml; Sigma-Aldrich) in PBS, then incubated for 6 hours at 37° C. The enzyme reaction was stopped by adding 2 microliters of 1,10-phenathroline (Sigma-Aldrich) in methanol (180 mg/ml). The sample of sera was diluted 3-fold and used in ELISA.

The following examples are provided as further clarification of the scope of the present invention. The following examples and any equivalents are disclosed.

Blood samples were drawn from the patients' median cubital veins. The samples of serum were collected. Serum was dispensed out into 100 microliters aliquotes and stored at −40° C.

EXAMPLE 1

Diagnoses of patients with lung cancer were established on the basis of the following parameters: clinical examination and confirmation by biopsy. The group consisted of 8 patients with cancer, comprising 4 patients with SCLC, stages T2b-T3b, and 4 patients with NSCLC stages T2a-T3a.

ELISA of samples from lung cancer patients was performed according to the method and procedure described herein. Samples wherein the optical density (OD) exceeded the negative control by more than 30% were considered positive.

Results:

Using the following sequences as the ligand: SEQ ID NO: 1, SEQ ID NO: 2, SEQ ID NO: 3, SEQ ID NO: 4, all 8 samples from lung cancer patients were positive. After incubation of the 8 samples from lung cancer patients, at a final dilution of 1:100 with carboxypeptidase B, all 8 samples from lung cancer patients, as well as the positive control, became negative. Using the following sequences as the ligand: SEQ ID NO: 5 and SEQ ID NO: 6 in an ELISA, all 8 samples from lung cancer patients were not differing from positive and negative controls. The OD of these samples did not exceed OD of the negative control plus 30%.

Conclusion:

There is strong correlation between existing lung cancer and a positive value in ELISA according to the present invention. The treatment of the samples by carboxypeptidase B confirms that only C-terminal lysine of damaged IgG or fragments thereof takes part in the binding of damaged IgG or/and fragments with a free C-terminal lysine thereof to: SEQ ID NO: 1, SEQ ID NO: 2, SEQ ID NO:3, SEQ ID NO: 4.

ELISA using SEQ ID NO: 5 and SEQ ID NO: 6 did not reveal any difference between the negative control and samples from lung cancer patients, whereas SEQ ID NO: 5 and SEQ ID NO: 6 have only 2 kringles, meaning that at least 3 kringles having a conservative amino acid sequence—Asn-Tyr-Cys-Arg-Asn-Pro-Asp (SEQ ID NO: 7)—are required for detecting damaged IgG or fragments with a free C-terminal lysine thereof.

EXAMPLE 2

Diagnoses of patients with breast cancer were established on the basis of the following parameters: clinical examination and confirmation by biopsy. The group consisted of 7 patients with breast cancer, stages T2a-T3a.

ELISA of samples from breast cancer patients was performed according to the methods and procedures described herein. Samples where the optical density (OD) exceeded the negative control by more than 30% were considered positive.

Results:

Using the following sequences as the ligand: SEQ ID NO: 1, SEQ ID NO: 2, SEQ ID NO: 3, SEQ ID NO: 4, all 7 samples from breast cancer patients were positive. After incubation of the 8 samples from breast cancer patients, at a final dilution of 1:100 with carboxypeptidase B, all 8 samples from breast cancer patients, as well as the positive control, became negative.

Using the following sequences as the ligand: SEQ ID NO: 5 and SEQ ID NO: 6 in an ELISA, all 7 samples from breast cancer patients were not differing from positive and negative controls. The OD of these samples did not exceed the OD of the negative control plus 30%.

Conclusion:

There is strong correlation between existing breast cancer and positive value in ELISA of the present invention. The treatment of the samples by carboxypeptidase B means that only C-terminal lysine of damaged IgG or fragments thereof plays a part in the binding of damaged IgG or/and fragments with a free C-terminal lysine thereof to SEQ ID NO: 1, SEQ ID NO: 2, SEQ ID NO: 3, SEQ ID NO: 4. ELISA using SEQ ID NO: 5 and SEQ ID NO: 6 did not reveal any difference between negative control and the samples from breast cancer patients. SEQ ID NO: 5 and SEQ ID NO: 6 have only 2 kringles, which indicates that at least 3 kringles having a conservative amino acid sequence—Asn-Tyr-Cys-Arg-Asn-Pro-Asp (SEQ ID NO: 7)—are needed for detecting damaged IgG or fragments with a free C-terminal lysine thereof.

EXAMPLE 3

Diagnoses of patients with colorectal cancer were established on the basis of the following parameters: clinical examination and confirmation by biopsy. The group consisted of 8 patients with colorectal cancer, stages T2a-T3b.

ELISA of samples from colorectal cancer patients was performed according to the methods and procedures described herein. Samples where the optical density (OD) exceeded the negative control by more than 30% were considered positive.

Results:

Using the following sequences as the ligand: SEQ ID NO: 1, SEQ ID NO: 2, SEQ ID NO: 3, SEQ ID NO: 4, all 8 samples from colorectal cancer patients were positive. After incubation of the 8 samples from colorectal cancer patients, at a final dilution of 1:100 with carboxypeptidase B, all 8 samples from colorectal cancer patients as well as the positive control became negative.

Using the following sequences as the ligand: SEQ ID NO: 5 and SEQ ID NO: 6 in an ELISA, all 8 samples from colorectal cancer patients were not differing from positive and negative controls. The OD of these samples did not exceed the OD of the negative control plus 30%.

Conclusion:

There is a strong correlation between existing colorectal cancer and positive value in ELISA according to the present invention. The treatment of the samples by carboxypeptidase B means that only C-terminal lysine of damaged IgG or fragments thereof plays a part in the binding of damaged IgG or/and fragments with a free C-terminal lysine thereof to SEQ ID NO: 1, SEQ ID NO: 2, SEQ ID NO: 3, SEQ ID NO: 4. ELISA using SEQ ID NO: 5 and SEQ ID NO: 6 did not reveal any difference between the negative control and the samples from colorectal cancer patients. SEQ ID NO: 5 and SEQ ID NO: 6 have only 2 kringles, indicating that at least 3 kringles having a conservative amino acid sequence—Asn-Tyr-Cys-Arg-Asn-Pro-Asp (SEQ ID NO: 7)—are required for detecting damaged IgG or fragments with a free C-terminal lysine thereof.

EXAMPLE 4

Diagnoses of patients with ovarian cancer were established on the basis of the following parameters: clinical examination and confirmation by biopsy. The group consisted of 6 patients with ovarian cancer, stages T2c-T3a.

ELISA of samples from ovarian cancer patients was performed according to the method and procedure described the present invention. The samples where the optical density (OD) exceeded the negative control by more than 30% were considered positive.

Results:

Using the following sequences as the ligand: SEQ ID NO: 1, SEQ ID NO: 2, SEQ ID NO: 3, SEQ ID NO: 4, all 6 samples from ovarian cancer patients were positive. After incubation of the 6 samples from ovarian cancer patients, at a final dilution of 1:100 with carboxypeptidase B, all 6 samples from ovarian cancer patients, as well as the positive control, became negative. Using the following sequences as the ligand: SEQ ID NO: 5 and SEQ ID NO: 6 in an ELISA, all 6 samples from ovarian cancer patients were not differing from positive and negative controls. The OD of these samples did not exceed the OD of the negative control plus 30%.

Conclusion:

There is strong correlation between existing ovarian cancer and positive value in ELISA of the present invention. The treatment of the samples by carboxypeptidase B means that only C-terminal lysine of damaged IgG or fragments thereof plays a part in the binding of damaged IgG or/and fragments with a free C-terminal lysine thereof to SEQ ID NO: 1, SEQ ID NO: 2, SEQ ID NO: 3, SEQ ID NO: 4. ELISA using SEQ ID NO: 5 and SEQ ID NO: 6 did not reveal any difference between the negative control and the samples from ovarian cancer patients. SEQ ID NO: 5 and SEQ ID NO: 6 have only 2 kringles, indicating that at least 3 kringles having a conservative amino acid sequence—Asn-Tyr-Cys-Arg-Asn-Pro-Asp (SEQ ID NO: 7)—are needed for detecting damaged IgG or fragments with a free C-terminal lysine thereof.

EXAMPLE 5

Diagnoses of patients with prostate cancer were established on the basis of the following parameters: clinical examination, transrectal ultrasonography, and confirmation by biopsy. The group consisted of 10 patients with prostate cancer, stages T2a-T3a.

ELISA of samples from prostate cancer patients was performed according to the method and procedure described the present invention. The samples where the optical density (OD) exceeded the negative control by more than 30% were considered positive.

Results:

Using the following sequences as the ligand: SEQ ID NO: 1, SEQ ID NO: 2, SEQ ID NO: 3, SEQ ID NO: 4, all 10 samples from prostate cancer patients were positive. After incubation of the 10 samples from prostate cancer patients, at a final dilution of 1:100 with carboxypeptidase B, all 10 samples from prostate cancer patients, as well as the positive control, became negative.

Using the following sequences as the ligand: SEQ ID NO: 5 and SEQ ID NO: 6 in an ELISA, all 10 samples from prostate cancer patients were not differing from positive and negative controls.

Conclusion:

There is strong correlation between existing prostate cancer and a positive value in ELISA according to the present invention. The treatment of the samples by carboxypeptidase B means that only C-terminal lysine of damaged IgG or fragments thereof plays a part the binding of damaged IgG and/or fragments with a free C-terminal lysine thereof to SEQ ID NO: 1, SEQ ID NO: 2, SEQ ID NO: 3, SEQ ID NO: 4. ELISA using SEQ ID NO: 5 and SEQ ID NO: 6 did not reveal any difference between the negative control and the samples from prostate cancer patients. SEQ ID NO: 5 and SEQ ID NO: 6 have only 2 kringles, indicating that at least 3 kringles having a conservative amino acid sequence—Asn-Tyr-Cys-Arg-Asn-Pro-Asp (SEQ ID NO: 7)—are needed for detecting damaged IgG or fragments with a free C-terminal lysine thereof.

In addition to the method for detecting damaged immunoglobulins G (IgG), or fragments thereof, having a free C-terminal lysine, the present invention further comprises a kit for detecting damaged immunoglobulins G (IgG) and/or fragments thereof having a free C-terminal lysine, in a human blood sample. The kit comprises the following components: (1) a 96-well plastic immunological plate coated by at least one fragment of plasminogen comprising SEQ. ID. NO. 1-4, (2) a positive control sample, said positive control sample comprising damaged IgG and/or fragments thereof with a free C-terminal lysine, (3) a negative control sample, said negative control sample comprising an absence of damaged IgG and/or fragments thereof having a C-terminal lysine, (4) and one or more mice monoclonal antibodies to human IgG, said mice monoclonal antibodies being conjugated with a horseradish peroxidase.

The kit may be used for analyzing a test subject that provides the human blood sample, analyzing that test subject's blood sample for lung cancer, breast cancer, colorectal cancer, ovarian cancer, and/or prostate cancer using the same or equivalent methods as described hereinabove.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A method for detecting damaged immunoglobulins G (IgG), or fragments thereof, having a free C-terminal lysine, the method comprising:
obtaining a human blood sample,
contacting said human blood sample with plasminogen consisting of one sequence of SEQ ID NO's: 1-4, wherein each sequence of SEQ ID NO's: 1-4 contains at least three copies of SEQ ID NO: 7 within the sequence of SEQ ID NO's: 1-4, and
detecting complexes comprising said plasminogen bound to the damaged IgG, or fragments thereof, having the free C-terminal lysine,
said detecting comprising comparing an expression of the contacted human blood sample to a positive control and a negative control,
said human blood sample being retrieved from an individual having lung cancer, breast cancer, colorectal cancer, ovarian cancer, or prostate cancer.

2. The method according to claim 1, wherein said human blood sample is serum or plasma.

3. The method of claim 1, wherein said contacting comprises contacting said blood sample with a solid support, wherein said one or more fragments of plasminogen are immobilized on a surface of said solid support.

4. The method of claim 1, wherein said detecting further comprises using an enzyme-linked immunosorbent assay (ELISA).

5. The method according to claim 1, wherein said positive control comprises damaged IgG, or fragments thereof, having a free C-terminal lysine.

6. The method according to claim 1, wherein said negative control comprises an absence of damaged IgG, or fragments thereof, with a free C-terminal lysine.

7. The method according to claim 1, the method being performed on an automated reading device.

8. The method according to claim 1, wherein said contacting is performed manually.

9. The method according to claim 1, wherein a 30-percent increase in a level of damaged IgG, or fragments thereof, having a free C-terminal lysine relative to said negative control is indicative of lung cancer, breast cancer, colorectal cancer, ovarian cancer, or prostate cancer.

* * * * *

SEQUENCE LISTING

```
<160> NUMBER OF SEQ ID NOS: 7

<210> SEQ ID NO 1
<211> LENGTH: 561
<212> TYPE: PRT
<213> ORGANISM: Homo sapiens

<400> SEQUENCE: 1

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175
```

```
Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
        355                 360                 365

Thr Ser Ser Thr Thr Thr Thr Gly Lys Lys Cys Gln Ser Trp Ser Ser
    370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
        435                 440                 445

Val Leu Leu Pro Asp Val Glu Thr Pro Ser Glu Glu Asp Cys Met Phe
450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
        515                 520                 525

Pro Arg Lys Leu Tyr Asp Tyr Cys Asp Val Pro Gln Cys Ala Ala Pro
    530                 535                 540

Ser Phe Asp Cys Gly Lys Pro Gln Val Glu Pro Lys Lys Cys Pro Gly
545                 550                 555                 560

Arg

<210> SEQ ID NO 2
<211> LENGTH: 484
<212> TYPE: PRT
<213> ORGANISM: Homo sapiens
```

```
<400> SEQUENCE: 2

Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
            35                  40                  45

Glu Gly Leu Glu Glu Asn Tyr Cys Arg Asn Pro Asp Asn Asp Pro Gln
50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
            115                 120                 125

Pro Asn Lys Asn Leu Lys Lys Asn Tyr Cys Arg Asn Pro Asp Arg Glu
            130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
            195                 200                 205

His Thr His Asn Arg Thr Pro Glu Asn Phe Pro Cys Lys Asn Leu Asp
            210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
            245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
            275                 280                 285

Tyr Arg Gly Thr Ser Ser Thr Thr Thr Gly Lys Lys Cys Gln Ser
            290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
            325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
            355                 360                 365

Pro Pro Val Val Leu Leu Pro Asp Val Glu Thr Pro Ser Glu Glu Asp
            370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
```

```
                405             410             415
His Ser Ile Phe Thr Pro Glu Thr Asn Pro Arg Ala Gly Leu Glu Lys
            420             425             430

Asn Tyr Cys Arg Asn Pro Asp Gly Asp Val Gly Gly Pro Trp Cys Tyr
            435             440             445

Thr Thr Asn Pro Arg Lys Leu Tyr Asp Tyr Cys Asp Val Pro Gln Cys
450             455             460

Ala Ala Pro Ser Phe Asp Cys Gly Lys Pro Gln Val Glu Pro Lys Lys
465             470             475             480

Cys Pro Gly Arg

<210> SEQ ID NO 3
<211> LENGTH: 370
<212> TYPE: PRT
<213> ORGANISM: Homo sapiens

<400> SEQUENCE: 3

Lys Val Tyr Leu Ser Glu Cys Lys Thr Gly Asn Gly Lys Asn Tyr Arg
1               5               10              15

Gly Thr Met Ser Lys Thr Lys Asn Gly Ile Thr Cys Gln Lys Trp Ser
            20              25              30

Ser Thr Ser Pro His Arg Pro Arg Phe Ser Pro Ala Thr His Pro Ser
            35              40              45

Glu Gly Leu Glu Glu Asn Tyr Cys Arg Asn Pro Asp Asn Asp Pro Gln
        50              55              60

Gly Pro Trp Cys Tyr Thr Thr Asp Pro Glu Lys Arg Tyr Asp Tyr Cys
65              70              75              80

Asp Ile Leu Glu Cys Glu Glu Cys Met His Cys Ser Gly Glu Asn
                85              90              95

Tyr Asp Gly Lys Ile Ser Lys Thr Met Ser Gly Leu Glu Cys Gln Ala
            100             105             110

Trp Asp Ser Gln Ser Pro His Ala His Gly Tyr Ile Pro Ser Lys Phe
            115             120             125

Pro Asn Lys Asn Leu Lys Lys Asn Tyr Cys Arg Asn Pro Asp Arg Glu
        130             135             140

Leu Arg Pro Trp Cys Phe Thr Thr Asp Pro Asn Lys Arg Trp Glu Leu
145             150             155             160

Cys Asp Ile Pro Arg Cys Thr Thr Pro Pro Ser Ser Gly Pro Thr
                165             170             175

Tyr Gln Cys Leu Lys Gly Thr Gly Glu Asn Tyr Arg Gly Asn Val Ala
            180             185             190

Val Thr Val Ser Gly His Thr Cys Gln His Trp Ser Ala Gln Thr Pro
            195             200             205

His Thr His Asn Arg Thr Pro Glu Asn Phe Pro Cys Lys Asn Leu Asp
        210             215             220

Glu Asn Tyr Cys Arg Asn Pro Asp Gly Lys Arg Ala Pro Trp Cys His
225             230             235             240

Thr Thr Asn Ser Gln Val Arg Trp Glu Tyr Cys Lys Ile Pro Ser Cys
                245             250             255

Asp Ser Ser Pro Val Ser Thr Glu Gln Leu Ala Pro Thr Ala Pro Pro
            260             265             270

Glu Leu Thr Pro Val Val Gln Asp Cys Tyr His Gly Asp Gly Gln Ser
            275             280             285

Tyr Arg Gly Thr Ser Ser Thr Thr Thr Thr Gly Lys Lys Cys Gln Ser
```

```
                    290                 295                 300
Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
                340                 345                 350

Cys Asn Leu Lys Lys Cys Ser Gly Thr Glu Ala Ser Val Val Ala Pro
            355                 360                 365

Pro Pro
    370

<210> SEQ ID NO 4
<211> LENGTH: 259
<212> TYPE: PRT
<213> ORGANISM: Homo sapiens

<400> SEQUENCE: 4

Tyr Leu Ser Glu Cys Lys Thr Gly Asn Gly Lys Asn Tyr Arg Gly Thr
1               5                   10                  15

Met Ser Lys Thr Lys Asn Gly Ile Thr Cys Gln Lys Trp Ser Ser Thr
                20                  25                  30

Ser Pro His Arg Pro Arg Phe Ser Pro Ala Thr His Pro Ser Glu Gly
            35                  40                  45

Leu Glu Glu Asn Tyr Cys Arg Asn Pro Asp Asn Asp Pro Gln Gly Pro
        50                  55                  60

Trp Cys Tyr Thr Thr Asp Pro Glu Lys Arg Tyr Asp Tyr Cys Asp Ile
65                  70                  75                  80

Leu Glu Cys Glu Glu Glu Cys Met His Cys Ser Gly Glu Asn Tyr Asp
                85                  90                  95

Gly Lys Ile Ser Lys Thr Met Ser Gly Leu Glu Cys Gln Ala Trp Asp
                100                 105                 110

Ser Gln Ser Pro His Ala His Gly Tyr Ile Pro Ser Lys Phe Pro Asn
            115                 120                 125

Lys Asn Leu Lys Lys Asn Tyr Cys Arg Asn Pro Asp Arg Glu Leu Arg
130                 135                 140

Pro Trp Cys Phe Thr Thr Asp Pro Asn Lys Arg Trp Glu Leu Cys Asp
145                 150                 155                 160

Ile Pro Arg Cys Thr Thr Pro Pro Ser Ser Gly Pro Thr Tyr Gln
                165                 170                 175

Cys Leu Lys Gly Thr Gly Glu Asn Tyr Arg Gly Asn Val Ala Val Thr
            180                 185                 190

Val Ser Gly His Thr Cys Gln His Trp Ser Ala Gln Thr Pro His Thr
        195                 200                 205

His Asn Arg Thr Pro Glu Asn Phe Pro Cys Lys Asn Leu Asp Glu Asn
    210                 215                 220

Tyr Cys Arg Asn Pro Asp Gly Lys Arg Ala Pro Trp Cys His Thr Thr
225                 230                 235                 240

Asn Ser Gln Val Arg Trp Glu Tyr Cys Lys Ile Pro Ser Cys Asp Ser
                245                 250                 255

Ser Pro Val

<210> SEQ ID NO 5
<211> LENGTH: 173
<212> TYPE: PRT
```

<213> ORGANISM: Homo sapiens

<400> SEQUENCE: 5

```
Cys Met His Cys Ser Gly Glu Asn Tyr Asp Gly Lys Ile Ser Lys Thr
1               5                   10                  15

Met Ser Gly Leu Glu Cys Gln Ala Trp Asp Ser Gln Ser Pro His Ala
            20                  25                  30

His Gly Tyr Ile Pro Ser Lys Phe Pro Asn Lys Asn Leu Lys Lys Asn
        35                  40                  45

Tyr Cys Arg Asn Pro Asp Arg Glu Leu Arg Pro Trp Cys Phe Thr Thr
    50                  55                  60

Asp Pro Asn Lys Arg Trp Glu Leu Cys Asp Ile Pro Arg Cys Thr Thr
65                  70                  75                  80

Pro Pro Pro Ser Ser Gly Pro Thr Tyr Gln Cys Leu Lys Gly Thr Gly
                85                  90                  95

Glu Asn Tyr Arg Gly Asn Val Ala Val Thr Val Ser Gly His Thr Cys
            100                 105                 110

Gln His Trp Ser Ala Gln Thr Pro His Thr His Asn Arg Thr Pro Glu
        115                 120                 125

Asn Phe Pro Cys Lys Asn Leu Asp Glu Asn Tyr Cys Arg Asn Pro Asp
    130                 135                 140

Gly Lys Arg Ala Pro Trp Cys His Thr Thr Asn Ser Gln Val Arg Trp
145                 150                 155                 160

Glu Tyr Cys Lys Ile Pro Ser Cys Asp Ser Ser Pro Val
                165                 170
```

<210> SEQ ID NO 6
<211> LENGTH: 192
<212> TYPE: PRT
<213> ORGANISM: Homo sapiens

<400> SEQUENCE: 6

```
Val Gln Asp Cys Tyr His Gly Asp Gly Gln Ser Tyr Arg Gly Thr Ser
1               5                   10                  15

Ser Thr Thr Thr Thr Gly Lys Lys Cys Gln Ser Trp Ser Ser Met Thr
            20                  25                  30

Pro His Arg His Gln Lys Thr Pro Glu Asn Tyr Pro Asn Ala Gly Leu
        35                  40                  45

Thr Met Asn Tyr Cys Arg Asn Pro Asp Ala Asp Lys Gly Pro Trp Cys
    50                  55                  60

Phe Thr Thr Asp Pro Ser Val Arg Trp Glu Tyr Cys Asn Leu Lys Lys
65                  70                  75                  80

Cys Ser Gly Thr Glu Ala Ser Val Val Ala Pro Pro Val Val Leu
                85                  90                  95

Leu Pro Asp Val Glu Thr Pro Ser Glu Glu Asp Cys Met Phe Gly Asn
            100                 105                 110

Gly Lys Gly Tyr Arg Gly Lys Arg Ala Thr Thr Val Thr Gly Thr Pro
        115                 120                 125

Cys Gln Asp Trp Ala Ala Gln Glu Pro His Arg His Ser Ile Phe Thr
    130                 135                 140

Pro Glu Thr Asn Pro Arg Ala Gly Leu Glu Lys Asn Tyr Cys Arg Asn
145                 150                 155                 160

Pro Asp Gly Asp Val Gly Gly Pro Trp Cys Tyr Thr Thr Asn Pro Arg
                165                 170                 175

Lys Leu Tyr Asp Tyr Cys Asp Val Pro Gln Cys Ala Ala Pro Ser Phe
```

```
                    180              185              190

<210> SEQ ID NO 7
<211> LENGTH: 7
<212> TYPE: PRT
<213> ORGANISM: Homo sapiens

<400> SEQUENCE: 7

Asn Tyr Cys Arg Asn Pro Asp
1               5
```